United States Patent [19]

Spencer

[11] Patent Number: 4,705,771
[45] Date of Patent: * Nov. 10, 1987

[54] PROCESS AND CATALYST FOR THE PRODUCTION OF FORMALDEHYDE FROM METHANE

[75] Inventor: Nicholas D. Spencer, Washington, D.C.

[73] Assignee: W. R. Grace & Co., New York, N.Y.

[*] Notice: The portion of the term of this patent subsequent to Aug. 19, 2003 has been disclaimed.

[21] Appl. No.: 816,506

[22] Filed: Jan. 6, 1986

Related U.S. Application Data

[62] Division of Ser. No. 723,680, Apr. 16, 1985, Pat. No. 4,607,127.

[51] Int. Cl.$^4$ .................. B01J 21/08; B01J 31/00; C01B 33/12
[52] U.S. Cl. .................. 502/255; 502/171; 423/335; 423/338; 423/339
[58] Field of Search ............. 502/255, 171; 423/335, 423/338, 339

[56] References Cited

U.S. PATENT DOCUMENTS

| | | | |
|---|---|---|---|
| 2,102,160 | 12/1937 | Nashan | 568/482 |
| 2,316,260 | 4/1943 | Lee et al. | 196/52 |
| 2,376,668 | 5/1945 | Derby | 568/482 X |
| 2,381,825 | 8/1945 | Lee et al. | 196/52 |
| 2,406,614 | 8/1946 | Lee et al. | 196/52 |
| 2,625,519 | 12/1952 | Hartig | 568/482 X |
| 3,956,185 | 5/1976 | Yogi et al. | 502/255 X |
| 3,996,294 | 12/1976 | Imre et al. | 260/604 R |
| 4,243,613 | 1/1981 | Brockhaus et al. | 568/482 |
| 4,368,345 | 1/1983 | Dickinson | 502/255 X |
| 4,428,862 | 1/1984 | Ward | 502/255 X |

FOREIGN PATENT DOCUMENTS

| | | | |
|---|---|---|---|
| 0031243 | 7/1981 | European Pat. Off. | 502/255 |
| 1940259 | 10/1970 | Fed. Rep. of Germany | 568/482 |
| 2404738 | 8/1975 | Fed. Rep. of Germany | 568/482 |
| 2404737 | 8/1975 | Fed. Rep. of Germany | 568/482 |
| 5892629 | 11/1981 | Japan | 568/482 |
| 1244001 | 8/1971 | United Kingdom | 568/482 |
| 1398385 | 6/1975 | United Kingdom | 568/482 |

OTHER PUBLICATIONS

Partial Oxidation of Methane by $NO_2$ and ZnO on $SiO_2$, Liu et al, J. Am. Chem. Soc., 1984, vol. 106, #15, p. 4117.

Partial Oxidation of Methane by $NO_x$ ones ZnO $O_3$ supported on $SiO_2$, Liu et al, Dept. of Chem., Texas A & M U., Coll. St., Tex., J. Chem. Soc. Chem. Commun., 1982, pp. 78–79.

Primary Examiner—Andrew Metz
Assistant Examiner—William G. Wright
Attorney, Agent, or Firm—Edward J. Cabic

[57] ABSTRACT

Formaldehyde is made from methane and a molecular oxygen containing gas by using a silica supported catalyst having less than 350 parts per million by weight of sodium and having a catalytically effective amount of $MoO_3$. The low sodium form of the silica support can be made by washing silica gel or precipitated silica, by using a fumed silica or by making an ultrapure form of silica having a silica purity of at least 99.99% silica. The ultrapure form can be made by the hydrolysis of silicon tetraalkoxides. In general, the lower the sodium level, the better is the catalyst.

7 Claims, No Drawings

PROCESS AND CATALYST FOR THE PRODUCTION OF FORMALDEHYDE FROM METHANE

This is a division of application Ser. No. 723,680, filed Apr. 16, 1985, now U.S. Pat. No. 4,607,127.

CROSS-REFERENCE TO RELATED APPLICATION

Application Ser. No. 862,190 filed June 6, 1986 is a continuation of application Ser. No. 723,681 filed Apr. 16, 1985, now abondaned describes and claims another catalyst which can be used in the present process invention.

BACKGROUND OF THE INVENTION

1. Field of the Invention

This invention relates to a highly selective method of producing formaldehyde, HCHO, by the partial oxidation of methane using a special type of catalyst and to a unique, highly selective formaldehyde-forming catalyst.

2. Description of the Previously Published Art

The major commercial process to make formaldehyde is from methanol. This involves the steam reforming of methane with high grade heat to convert the methane into syn gas. The syn gas is reacted to form methanol while giving off low grade heat. Then the methanol is oxidized to formaldehyde while giving off additional low grade heat. This synthesis procedure requires multiple steps and it involves poor energy usage.

In the past a small fraction of formaldehyde was made by the partial oxidation of lower petroleum hydrocarbons which involved the partial oxidation of the hydrocarbon gas with air or oxygen under pressure, followed by rapid cooling, condensation, and absorption of the products in water to give a crude solution, which must then be refined to separate formaldehyde from the other reaction products such as methanol, acetaldehyde, propyl alcohol, propionaldehyde, and orgainc acids. Formaldehyde is isolated as a dilute solution, which must be concentrated to market strength. Propane and butane are the basic hydrocarbon raw materials for formaldehyde. Products manufactured, by oxidation of propane and butane include formaldehyde, acetaldehyde, acetone, propionaldehyde, methanol, n-propyl alcohol, isopropyl alcohol, and butyl alcohols.

The German Offenlegungsschrift No. 2,404,738 to Bayer discloses oxidizing methane to formaldehyde by using many different types of metal oxides which may be placed on many different types of supports. The metal oxides are in Groups V, VI and/or VII of the Periodic Table. Among those listed are oxides of vanadium, niobium, tantalum, chromium, uranium, molybdenum, tungsten, manganese, technetium and rhenium, mixtures of these oxides with each other, and mixtures of these oxides with other oxides such as silica, alumina, iron oxide, calcium oxide, magnesia, sodium oxide or potassium oxide. In the first example using methane, the catalyst is 10 wt % Mo as $MoO_3$ on silica.

This reference is not helpful in finding an optimum methane conversion catalyst. It provides no attention as to the criticality of the support. It groups silica with alumina and other metal oxides yet, as will be shown in the following examples, alumina when used as a support is not as effective as the catalyst of the present invention.

Furthermore the Bayer reference provides no attention to the criticality of having a low sodium concentration. As will be shown in the following Comparison Example 1 and reported in Table 1, even when the Baver molybdenum oxide-silica combination is used, as in Example 1 of the German patent application, the selectivity to formaldehyde is lower than the obtained with the present invention. This difference in result is believed due to the significant levels of sodium which can be present in silica. Sodium is present in most forms of silica that are synthesized in aqueous media because the conventional starting materials contain sodium. Offenlegungschrift No. 2404738 goes so far as to specify that up to 5 wt % $Na_2O$ may be present in the working catalyst. As will be shown in Examples 7–10, sodium in these concentrations has a profoundly deleterious effect on selectivity to formaldehyde in the partial oxidation of methane.

U.S. Pat. No. 3,996,294, to Imre et al and assigned to Bayer discloses the use of a silica catalyst which does not contain any molybdenum to produce formaldehyde from methane. As will be shown in the examples, a catalyst consisting purely of silica, such as Cabosil (a product of Cabot Corporation), exhibits a lower selectivity to formaldehyde than is obtained with the catalyst of the present invention. Some of the examples in the Imre et al patent employ catalysts made substantially of silica along with small amounts of other metal oxides. There is no example given of using molybdenum oxide, although, as in the companion German Offenlegungsschrift, there is a broad list of metal oxides which can be used, including oxides of aluminum, iron, vanadium, molybdenum, tungsten, calcium, magnesium, sodium or potassium with a specific reference that up to 5% of $Na_2O$ can be used.

Japanese Patent Publication No. 58-92629 discloses a $SiO_2$-$MoO_3$ catalyst, using $N_2O$ or oxygen as oxidants. They report negligible selectivity to methanol or formaldehyde in the case of $O_2$ oxidation. In the publication of Liu et al (J. Chem. Soc. Chem. Commun. 1982, 78 and J. Am. Chem. Soc. 1984, 106, 4117) a molybdena-silica catalyst is described, which also uses nitrous oxide for the partial oxidation of methane to formaldehyde and methanol. The use of $N_2O$ as an oxidant is prohibitively expensive. Also, the silica in the catalyst is a fumed silica which is an expensive form of silica.

British Pat. No. 1398385 discloses a methane partial oxidation catalyst consisting of $MoO_3$ and CuO in the absence of carrier or binder. The inventors state, however, that the presence of at least 2 vol. % of a higher hydrocarbon must be present for the process to be effective, and their principal oxygenated product is methanol. Formaldehyde selectivity reaches a maximum of 15.5%.

British Pat. No. 1244001 discloses several catalysts for the partial oxidation of hydrocarbons. All of these catalysts contain $MoO_3$. The inventors claim that the principal oxygenated product is methanol, and the maximum selectivity to formaldehyde is 8%.

3. Objects of the Invention

It is an object of this invention to produce formaldehyde from methane without the production of a large number of by-products so as to avoid the attendant separation problems.

It is a further object of this invention to partially oxidize methane to form formaldehyde.

It is a further object of this invention to convert methane to formaldehyde with high selectivity.

It is a further object of this invention to obtain a methane conversion catalyst which converts methane to formaldehyde with high selectivity.

It is a further object of this invention to produce a methane conversion catalyst with an ultrapure silica support having a low sodium concentration.

It is a further object of this invention to produce a methane conversion catalyst having a selectivity of greater than 40% to the formation of formaldehyde when operating at an oxygen consumption value of 3.2%.

These and further objects will become apparent as the description of the invention proceeds.

SUMMARY OF THE INVENTION

A catalytic process has been developed which converts methane to formaldehyde with high selectivity. It employs a catalyst which is made of molybdenum trioxide, $MoO_3$, supported on silicon dioxide containing low levels of sodium. The molybdenum trioxide is present in concentrations from a catalytically effective amount to 50 wt. % Mo, and especially preferred values are between about 0.5 wt. % and 15 wt. % Mo. Although higher $MoO_3$ loadings such as greater than 15 wt. % Mo could be used, such catalysts rapidly lose $MoO_3$ due to sublimation. Because this sublimation loss could have serious consequences on downstream processes, such high $MoO_3$ loadings are not preferred. The silica support can have a surface area in the range of 20-1000 $m^2/g$, and more preferably in the range of 30-600 $m^2/g$. The silica support should contain a low amount of sodium such as in the range of between 0 and 350 ppm Na, preferably between 0 ppm and 100 ppm Na and most preferably between 0 and 20 ppm Na or at a level of 1 ppm or less.

A novel $MoO_3$ containing catalyst which provides the highest selectivity for converting methane to formaldehyde utilizes an ultrapure silica support which has a silica content of at least 99.99 wt % silica and a sodium content of less than 50 ppm. More preferable forms have sodium contents of less than 4 ppm and more preferably less than 2 ppm. These catalysts provide very high turnover numbers on the order of 38 micromoles of formaldehyde per square meter of catalyst per hour. Such a turnover rate is approximately 6 times higher than similar $MoO_3$ loaded catalysts where the support is fumed silica. Higher turnover numbers are advantageous, since they allow reactors to be reduced in size, with a consequent decrease in capital outlay.

DESCRIPTION OF THE PREFERRED EMBODIMENTS

The present invention discloses the ability to have methane converted to formaldehyde with a high selectivity by reacting methane simultaneously with a molecular oxygen containing gas when employing a catalyst having a catalytically effective amount of $MoO_3$ on a silica support where the silica support is critically selected such that it has a sodium content of less than 350 ppm Na. As will be seen in the following examples, this encompasses a broad range of silica supports. Among the preferred silica supports is an ultrapure silica having a $SiO_2$ content of at least 99.99 wt %. This silica can be prepared by the hydrolysis of a silicon tetraalkoxide. A catalyst made from this ultrapure support is shown to have the highest selectivity and the highest turnover numbers.

The catalyst can be prepared by either the incipient wetness technique or by evaporation to dryness of a slurry of silica in a molybdenum-containing solution. In the incipient wetness technique particles of silica are impregnated by an amount of a molybdenum-containing solution equal to the pore volume of the silica being impregnated. In the evaporation to dryness technique the particles of silica are placed in a volume of aqueous molybdenum-containing solution and the solvent evaporated.

If the catalyst is in a powder form, it can be pelleted, crushed and screened to obtain uniform size particles for loading into the reactor. The size of the particles can be adjusted and selected depending on the geometry of the reactor.

The preferred form of molybdenum for impregnation is ammonium paramolybdate, which dissolves in water or in a very dilute hydrogen peroxide solution. Other possible molybdenum salts would include molybdenum oxalate and possibly phosphomolybdic acid.

The catalysts produced by either of these preferred methods have the molybdenum trioxide, $MoO_3$, present in concentrations between a catalytically effective amount which can be as low as 0.5 wt. % and 50 wt. % Mo, and especially preferred values are between 0.5 wt. % and 15 wt. % Mo. When catalysts are made with $MoO_3$ loadings higher than about 15 wt. % Mo, the catalysts rapidly lose some of the $MoO_3$ due to sublimation. These higher $MoO_3$ loaded catalysts are not preferred because the sublimed $MoO_3$ could travel to downstream processes where it would adversely affect these processes.

For the molybdenum trioxide-silica catalysts to be maximally selective for formaldehyde synthesis from methane, it appears the silica component must possess a low sodium level. This result may be achieved by using silica with an intrinsically low sodium level such as Cabosil, a product of Cabot Corporatio, or by removing sodium from a form of silica with an intrinsically high sodium level such as Intermediate Density ("ID") Silica Gel or a precipitated silica such as Sylox-15. Both of these products are made by the Davison Chemical Division of W. R. Grace & Co. A further way to achieve the low sodium level is to use an ultrapure form of silica which has a $SiO_2$ content of at least 99.99 wt %. This can be made, for example, by the hydrolysis of a silicon tetraalkoxide.

The silica should ultimately have a sodium content in a range of between 0 and 350 ppm Na, preferably between 0 ppm and 100 ppm Na and most preferably between 0 and 20 ppm Na or at a level of 1 ppm or less. As will be illustrated in Example 7-10, the presence of even small concentrations of sodium has a profoundly deleterious effect on the HCHO selectively of methane oxidation, when it is catalyzed by the $MoO_3$-$SiO_2$ system. The surface area of the silica is in the range of 20-1000 $m^2/g$, preferably between 30 $m^2/g$ and 600 $m^2/g$.

The catalyst can be used to oxidize methane to formaldehyde at temperatures preferably between 500° and 700° C., a variety of pressures including atmospheric, space velocities between 1,000 and 20,000 $hr^{-1}$ (GHSV at NTP) and gas compositions from 0.5% $O_2$ (as oxygen or air) in $CH_4$ to the upper explosion limit which is dependent on pressure and concentration of inerts as discussed by C. M. Cooper and P. J. Wiezevich, Ind. Eng. Chem., 21, (1929) 1210. Under optimal conditions, formaldehyde selectivities in excess of 90% (carbon basis) can be obtained.

The oxygen comsumption value is determined as the difference between the inlet and outlet oxygen concentrations. When operating at oxygen comsumption values of 3.2%, the catalysts made according to the present invention desirably have selectivities of greater than 40%.

The ultrapure silica support is preferably made by hydrolyzing an alcoholic solution of a silicon tetraalkoxide such as silicon tetraethoxide, followed by slow drying and calcination.

Having described the basic aspects our invention, the following examples are given to illustrate specific embodiments thereof.

EXAMPLE 1

This example illustrates the preparation of a catalyst using an ultrapure form of silica.

The ultrapure material was made by dissolving 104 g silicon tetraethoxide in 104 g ethanol. Concentrated ammonia solution was added to the mixture until the pH exceeded 9.0. Gellation began to occur immediately, and the supernatant was allowed to evaporate overnight. The gel was dried at 70° for 5 days in air, followed by calcination at 500° C. for 2 hours in air.

A catalyst was prepared by impregnating 5 g of the silica thus formed by incipient wetness with 0.158 g ammonium paramolybdate 4-hydrate and calcining at 482° C. for three hours. The resulting catalyst had a molybdenum loading of 1.6 wt % and a sodium level below the detection limit of inductively-coupled plasma analysis techniques. The BET surface area was 47 m$^2$/g. The catalyst was pressed together, crushed and screened to US 25-35.

EXAMPLE 2

This example illustrates the preparation of a catalyst using a fumed silica.

The catalyst was prepared by impregnating 50 g. of "Cabosil", a fumed silica made by Cabot Corp. with 10.82 g ammonium paramolybdate 4-hydrate by incipient wetness and calcining the impregnated product at 482° C. for 3 hours. The resulting catalyst has a molybdenum loading of 9.75 wt. % and a sodium level lower than 4 ppm. The surface area was approximately 210 m$^2$/g (BET). The catalyst was pressed together, crushed and screened to U. S. 25-35.

EXAMPLE 3

This example illustrates the preparation of a catalyst using an acid washed silica gel.

A 15 g portion of dry Davison "ID" silica gel, which has previously been washed in dilute H$_2$SO$_4$ solution having a pH of 3 at 100° C. for 2 days, was screened to US 25-35 and impregnated by immersion in a solution of 3.25 g ammonium paramolybdate 4-hydrate in 30 cc water, followed by evaporation to dryness and calcination at 600° C. for 4 hours. The resulting catalyst had a surface area of 232 m$^2$/g, a molybdenum loading of 8.63 wt. % and a sodium level less than 20 ppm.

COMPARISON EXAMPLE 1

This catalyst was prepared using a commercially available silica gel where the sodium content was not reduced.

A commercial grade silica gel, Davison "ID", manufactured by the Davison Chemical Division of W. R. Grace & Co. was used without further processing. A catalyst based on this material was prepared by following the method of Example 2 with the exception that the H$_2$SO$_4$ treatment, which lowers sodium content, was not carried out. The resulting catalyst had a molybdenum loading of 9.7 wt %, a sodium level of 520 ppm and a surface area of 282 m$^2$/g (BET). This example, in effect, is what one would produce by following Example 1 of the Bayer German Offenlegungsschrift No. 2,404,738. There Bayer makes no reference to the need to limit sodium content and consequently it is likely that the silica used has a relatively high sodium level. Supporting this interpretation is the statement on page 4 of the publication that up to 5 wt % Na$_2$O may be present in the working catalyst.

EXAMPLE 4

This example illustrates the preparation of a catalyst using an acid washed precipitated silica.

A 5 g sample of dry Davison Sylox-15 silica, which had previously been washed briefly at room temperature in dilute H$_2$SO$_4$ at a pH of 3, was impregnated by incipient wetness with 1.08 g ammonium paramolybdate 4-hydrate dissolved in water. The resulting solid was calcined at 482° C. for 3 hours, pressed together, washed and screened to US 25-35. The catalyst had a Mo loading of 9.9 wt. %, a sodium level of 310 ppm and a surface area of 164 m$^2$/g (BET).

EXAMPLE 5

This example illustrates the preparation of a comparison catalyst using alumina as a support.

In a mixture of 31 g hydrogen peroxide (30%) and 379 cc water was dissolved 69.4 g ammonium paramolybdate 4-hydrate. The solution was then mulled into 500 g of an alumina made according to the procedure of U. S. Pat. No. 4,154,812 and the paste extruded, dried overnight at 230° F., calcined for 3 hours at 900° F., crushed and screened to US 25-35. The catalyst had a Mo loading of 11.8 wt %, a sodium level of 290 ppm and a surface area of 180 m$^2$/g (BET).

EXAMPLE 6

This example sets forth the evaluation of the catalysts made in Examples 1-5, Comparison Example 1, pure Cabosil, and the ultrapure support material made in Example 1 without any MoO$_3$.

A 0.20 g (approx. 0.54 cc) sample of the screened catalyst was placed on a quartz frit in a ⅜" O.D. quartz tube and covered with 0.2 g US 25-35 screened quartz, which formed a preheating zone. A thermocouple was inserted into the bed such that its tip was at the entrance to the catalyst section.

Gas mixtures consisting of 95% methane and 5% oxygen and 90% methane and 10% oxygen, were passed through the tube at 1 atm, at gas hourly space velocities of 2500–10,000 hr$^{-1}$ (NTP) while the tube was heated to 575°, 600°, 625° and 650° C. The exit gases passed through heat traced Teflon ® lines to a gas chromatograph where formaldehyde and carbon dioxide were analyzed in a Poropak T column in series with a methanizer and flame ionization detector. Other gases were analyzed using a thermal conductivity detector with a carbosphere column. The methanizer had been calibrated for formaldehyde against the chromatropic acid method. See West, P. W. and Sen B., Z. Anal. Chem. 153 (1956) 177–183. The results are set forth in Table 1. In this table oxygen consumption is defined as the difference between the inlet and outlet oxygen concentrations at an operating pressure of 1 atm.

silica gel where no attempt was made to reduce the sodium content. At each of the $O_2$ consumption levels

TABLE 1

| Examples | Description | Mo % | HCHO SELECTIVITIES AT DIFFERENT VALUES OF $O_2$ CONSUMPTION | | | | | |
|---|---|---|---|---|---|---|---|---|
| | | | 0.1% | 0.2% | 0.5% | 1.0% | 2.4% | 3.2% |
| 1 | $MoO_3$ Ultrapure Silica | 1.6% | 90 | 88 | 85 | 78 | 66 | 59 |
| 2 | $MoO_3$ - Cabosil | 9.8 | 89 | 88 | 83 | 75 | 58 | 48 |
| 3 | $MoO_3$ - Acid Washed Silica Gel | 8.6 | 74 | 73 | 68 | 63 | 52 | 49 |
| 4 | $MoO_3$ - Acid Washed Sylox 15 | 9.9 | 83 | 82 | 72 | 63 | 49 | 41 |
| 5 | $MoO_3$ - Alumina | 11.8 | 0 | 0 | 0 | 0 | 0 | 0 |
| Comparison Ex. 1 | $MoO_3$ - Untreated Silica Gel[1] | 9.7 | 67 | 66 | 59 | 42 | 27 | 23 |
| | Pure Cabosil | 0 | 44 | 47 | 50 | 40 | 30 | 23 |
| | Ultrapure Silica | 0 | — | 40 | 31 | — | — | — |
| Literature Values* | | | | | | | | |
| BAYER 2404738 Example 1 | $MoO_3$ - Silica | 10 | — | — | — | — | 33 | — |
| U.S. 3,996,294 Example 1 | Silica | 0 | — | — | — | — | — | 38.1 |

*Data reported in patent applications
[1]prepared according to BAYER 2404738

As the methane oxidation reaction continues to proceed further, as measured by the higher oxygen consumption, the selectivity to the formaldehyde intermediate decreases because more of the final end products of CO, $CO_2$ and $H_2O$ are formed. Within the range of conditions studied, the selectivity appeared to be a function of oxygen consumption, irrespective of the combination of temperatures and space velocities necessary to achieve this consumption.

The results show that the silica supported catalysts according to the present invention is Examples 1–4 are superior catalysts with selectivities as high as 90% whereas the alumina supported catalyst in Example 5 which does not contain silica is an unacceptable catalyst with no detectable formaldehyde synthesis activity.

Pure silica in the form of Cabosil showed some activity as an oxidation catalyst, but displayed a much lower selectivity to formaldehyde than the $MoO_3$ containing catalyst according to the present invention in Examples 1–4. Similarly just using ultrapure silica from Example 1 without any $MoO_3$ resulted in a poor catalyst with low selectivities.

Also presented in Table 1 are the two data points reported in Bayer German Offenlegungsschrift No. 2,404,738 (for 10 wt % Mo as $MoO_3$ on $SiO_2$) and in Imre et al. U.S. Pat. No. 3,996,294 for pure silica. From reading the patents, there is no indication of the criticality of having a low sodium content. In Comparison Example 1 a $MoO_3$-silica catalyst was made following these prior art teachings with a commercially available silica gel where no attempt was made to reduce the sodium content. At each of the $O_2$ consumption levels the selectivity of the catalyst of Comparison Example 1 is less than the levels obtained by using the low sodium catalyst according to the present invention.

The catalysts were also evaluated with a feed stream of 10% $O_2$ in methane, at 650° C., at 2500 $hr^{-1}$ (GHSV, NTP), and at 1 atm. The % methane conversion as determined by gas chromatography and the turnover number in micromoles methane converted per square meter of catalyst per hour (a measure of specific activity) are set forth in Table 2.

TABLE 2

| Examples | Description | Mo % | BET Surface Area $m^2/g$ | $CH_4$ Conversion % | Turnover Number micromoles $CH_4$ converted per $m^2$ catalyst per hour |
|---|---|---|---|---|---|
| 1 | $MoO_3$ - Ultrapure Silica | 1.6 | 47 | 5.9 | 37.9 |
| 2 | $MoO_3$ - Cabosil | 9.8 | 210 | 4.3 | 6.18 |
| 3 | $MoO_3$ - Acid Washed Silica Gel | 8.6 | 232 | 6.1 | 7.93 |
| 4 | $MoO_3$ - Acid Washed Sylox 15 | 9.9 | 164 | 5.3 | 9.75 |
| 5 | $MoO_3$ - Alumina | 11.8 | 180 | 5.5 | 9.22 |
| Comparison Ex. 1 | $MoO_3$ - Untreated Silica Gel[1] | 9.7 | 282 | 3.4 | 3.64 |
| | Pure Cabosil | 0 | 312 | 2.2 | 2.13 |
| | Ultrapure Silica | 0 | 41 | 0.45 | 3.31 |

These results show that the ultrapure silica-supported molybdena catalyst has an exceptionally high specific activity. The molybdena-containing catalysts have activities which are higher than those of silica-only catalysts and the acid washed silica gel-supported molybdena catalyst has more than twice the specific activity of the "as received" silica gel-supported molybdena catalyst. The alumina-supported catalyst also has a high specific activity but as was set forth in Table 1, it produces no detectable formaldehyde and the methane is principally oxidized to carbon oxides and water.

EXAMPLE 7–10

These examples illustrate the effect of various concentrations of sodium on two types of silica supports.

Cabosil has less than 4 ppm Na and thus a sodium-loaded version was made by washing it in a dilute solution of sodium hydroxide having a pH of 10.2 at 100° C. Silica gel, on the other hand, contains substantial sodium as manufactured. Low-sodium versions were made by washing in dilute H₂SO₄ having a pH of 3 at different temperatures. The supports were made into catalysts using the method of Example 2 for the treated and untreated Cabosil and the method of Example 3 for the treated and untreated silica gels. The catalysts were tested according to the procedure in Example 6 and the results are set forth in Table 3.

TABLE 3

| Examples | Description | Mo % | Na (ppm) | HCHO Selectivity at 2.4% $O_2$ Consumption |
|---|---|---|---|---|
| 2 | $MoO_3$ - Cabosil | 9.8 | less than 4 | 58% |
| 7 | $MoO_3$ - Acid Washed (100° C.) Silica Gel | 8.6 | 20 | 52% |
| 8 | $MoO_3$ - Acid Washed (RT) Silica Gel | 9.8 | 300 | 39% |
| 9 | $MoO_3$ - Untreated Silica Gel | 9.7 | 520 | 27% |
| 10 | $MoO_3$ - Na—Loaded Cabosil | 9.4 | 3600 | 8% |
| BAYER 2404738 | $MoO_3$ - Silica (source unknown) | 10 | unknown | 33% |

Thus it can be observed that irrespective of the nature of the silica support, the presence of even small concentrations of sodium has a profoundly deleterious effect on the HCHO selectivity of methane oxidation when it is catalyzed by the $MoO_3$-$SiO_2$ system.

EXAMPLE 11 AND 12

These examples illustrate the efficiency of catalysts having low $MoO_3$ loadings on silica for the partial oxidation of methane.

Acid washed silica gel catalysts were prepared according to the method set forth in Example 3, with the exception that the Mo loadings were 1.8 and 10%. The catalysts were tested according to the general procedure in Example 6 but at conditions of a GSHV of 2500 hr$^{-1}$ at NTP, 1 atmosphere pressure, 10% $O_2$ in $CH_4$ and 650° C. The results are set forth in Table 4.

TABLE 4

| SELECTIVITY TO HCHO AND ACTIVITY FOR METHANE OXIDATION[1] OF $SiO_2$—$MoO_3$ BASED CATALYSTS AT SPACE VELOCITY OF 2500 hr$^{-1}$ (GHSV, NTP) AND 650° C. | | | | |
|---|---|---|---|---|
| Catalyst | Mo % | $CH_4$ Conversion % | Selectivity to Formaldehyde | HCHO Yield ($CH_4$ basis) × $10^{-4}$ |
| Example 11 | 1.8 | 6.4 | 35% | 224 |
| Example 12 | 10 | 6.2 | 15% | 93 |

[1]Gas composition 10% $O_2$, 90% $CH_4$

The activity as measured by methane conversion and formaldehyde yield under identical conditions is higher for the catalyst containing the lower level of molybdenum of 1.8%. Yield is defined as the product of selectivity and conversion.

It is understood that the foregoing detailed description is given merely by way of illustration and that many variations may be made therein without departing from the spirit of this invention.

What is claimed is:

1. A catalyst suitable for the partial oxidation of methane comprising $MoO_3$ on a silica support made by the hydrolysis of silicon tetraalkoxides and having a silica purity of at least 99.99% silica, a total impurity level less than 100 ppm, and having a low sodium content of less than 50 ppm, said amount of $MoO_3$ being at least a catalytically effective amount and up to an amount where the Mo content is about 50% by weight of the catalyst.

2. A catalyst according to claim 1, wherein the silica support has a BET nitrogen surface area of at least 20 m²/g.

3. A catalyst according to claim 1, wherein the sodium content is less than 4 ppm.

4. A catalyst according to claim 3 wherein the sodium content is less than 2 ppm.

5. A catalyst according to claim 4, wherein the sodium content is 1 ppm or less.

6. A catalyst according to claim 1, wherein the amount of $MoO_3$, expressed as wt % Mo, is an amount up to 15 wt % Mo.

7. A catalyst according to claim 6, wherein the amount of $MoO_3$ is from about 0.5-15 wt % Mo.

* * * * *